(12) United States Patent
Frankson et al.

(10) Patent No.: US 10,842,912 B2
(45) Date of Patent: Nov. 24, 2020

(54) FUNCTIONALIZED PEG FOR IMPLANTABLE MEDICAL DEVICES

(71) Applicant: Cardiac Pacemakers, Inc., St. Paul, MN (US)

(72) Inventors: Danielle Frankson, Dayton, MN (US); Joseph T. Delaney, Jr., Minneapolis, MN (US); David R. Wulfman, Minneapolis, MN (US); Adam McGraw, Mansfield, MA (US); Sarah M. Gruba, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 377 days.

(21) Appl. No.: 15/673,274

(22) Filed: Aug. 9, 2017

(65) Prior Publication Data

US 2018/0043056 A1  Feb. 15, 2018

Related U.S. Application Data

(60) Provisional application No. 62/372,753, filed on Aug. 9, 2016.

(51) Int. Cl.
*A61L 27/12* (2006.01)
*A61L 27/34* (2006.01)
(Continued)

(52) U.S. Cl.
CPC .............. *A61L 27/12* (2013.01); *A61L 27/04* (2013.01); *A61L 27/047* (2013.01); *A61L 27/06* (2013.01); *A61L 27/34* (2013.01); *A61L 27/54* (2013.01); *C08L 71/02* (2013.01); *A61F 2/86* (2013.01); *A61L 2300/102* (2013.01);
(Continued)

(58) Field of Classification Search
CPC .......... A61L 27/34; A61L 31/10; C08L 79/02; A61M 31/00; A61K 38/16
See application file for complete search history.

(56) References Cited

U.S. PATENT DOCUMENTS 4,179,337 A  12/1979  Davis et al.
5,488,954 A   2/1996  Sleva et al.
(Continued)

FOREIGN PATENT DOCUMENTS

CN  103079462 A  5/2013
EP    0633031 A1  1/1995
(Continued)

OTHER PUBLICATIONS

Vanderah, David J., et al. "Self-Assembled Monolayers of Methyl 1-Thiahexa(ethylene oxide) for the Inhibition of Protein Adsorption." Langmuir 18:4674-4680, 2002.
(Continued)

*Primary Examiner* — Dah-Wei D. Yuan
*Assistant Examiner* — Andrew J Bowman
(74) *Attorney, Agent, or Firm* — Faegre Drinker Biddle & Reath LLP

(57) ABSTRACT

A coating for a metal surface, the coating including poly (ethylene glycol) disposed on and covalently bonded directly to at least a portion of the metal surface, and a functional group grafted to at least a portion of the poly (ethylene glycol). The functional group is one of a bioactive functional group and an antimicrobial functional group.

20 Claims, 8 Drawing Sheets

(51) Int. Cl.
  *A61L 27/06* (2006.01)
  *C08L 71/02* (2006.01)
  *A61L 27/04* (2006.01)
  *A61L 27/54* (2006.01)
  *A61F 2/86* (2013.01)

(52) U.S. Cl.
  CPC ... *A61L 2300/214* (2013.01); *A61L 2300/404* (2013.01); *A61L 2300/412* (2013.01)

(56) References Cited

U.S. PATENT DOCUMENTS

| | | | |
|---|---|---|---|
| 6,451,003 | B1 | 9/2002 | Prosl et al. |
| 6,555,157 | B1 | 4/2003 | Hossainy |
| 6,617,027 | B2 | 9/2003 | Kim et al. |
| 6,669,980 | B2 | 12/2003 | Hansen |
| 6,793,960 | B1 | 9/2004 | Michal et al. |
| 7,037,332 | B2 | 5/2006 | Kutryk et al. |
| 7,322,965 | B2 | 1/2008 | Gibson et al. |
| 7,329,366 | B1 | 2/2008 | Gale et al. |
| 7,491,233 | B1 | 2/2009 | Ding et al. |
| 7,591,841 | B2 | 9/2009 | Hossainy et al. |
| 7,650,848 | B2 | 1/2010 | Brennan et al. |
| 8,131,376 | B1 | 3/2012 | Faraji et al. |
| 8,175,722 | B2 | 5/2012 | Parker et al. |
| 8,263,107 | B2 | 9/2012 | Pacetti et al. |
| 8,948,881 | B2 | 2/2015 | Fisk |
| 10,335,513 | B2 * | 7/2019 | Frankson ............... A61L 27/06 |
| 10,342,899 | B2 | 7/2019 | Delaney, Jr. et al. |
| 2001/0008931 | A1 | 7/2001 | Van Antwerp et al. |
| 2002/0019658 | A1 | 2/2002 | Munshi |
| 2003/0104028 | A1 | 6/2003 | Hossainy et al. |
| 2004/0044404 | A1 | 3/2004 | Stucke et al. |
| 2004/0167633 | A1 | 8/2004 | Wen et al. |
| 2006/0004432 | A1 | 1/2006 | Parker et al. |
| 2006/0008500 | A1 | 1/2006 | Chavan et al. |
| 2006/0057180 | A1 | 3/2006 | Chilkoti et al. |
| 2007/0250045 | A1 | 10/2007 | Trieu |
| 2008/0140152 | A1 | 6/2008 | Imran et al. |
| 2008/0312356 | A1 | 12/2008 | Kobrin et al. |
| 2009/0043369 | A1 | 2/2009 | Radeloff |
| 2009/0093879 | A1 | 4/2009 | Wawro et al. |
| 2009/0123516 | A1 | 5/2009 | Agrawal et al. |
| 2009/0247666 | A1 | 10/2009 | Yu et al. |
| 2010/0114225 | A1 | 5/2010 | Imran et al. |
| 2010/0152708 | A1 | 6/2010 | Li et al. |
| 2010/0198150 | A1 | 8/2010 | Michal et al. |
| 2011/0257702 | A1 | 10/2011 | Kara et al. |
| 2011/0306722 | A1 | 12/2011 | Lellouche et al. |
| 2013/0029421 | A1 | 1/2013 | Komvopoulos et al. |
| 2013/0098550 | A1 | 4/2013 | Sargeant et al. |
| 2014/0114435 | A1 | 4/2014 | Carpenter et al. |
| 2014/0172028 | A1 | 6/2014 | Meredith |
| 2014/0187666 | A1 | 7/2014 | Aizenberg et al. |
| 2014/0316482 | A1 | 10/2014 | Kane et al. |
| 2015/0283301 | A1 | 10/2015 | Semetey et al. |
| 2016/0038743 | A1 | 2/2016 | Foster et al. |
| 2017/0173223 | A1 | 6/2017 | Delaney, Jr. et al. |
| 2017/0360987 | A1 | 12/2017 | Frankson et al. |

FOREIGN PATENT DOCUMENTS

| | | | | |
|---|---|---|---|---|
| JP | | 2002505930 | A | 2/2002 |
| JP | | 2005523116 | A | 8/2005 |
| JP | | 2010537728 | A | 12/2010 |
| JP | | 201363322 | A | 4/2013 |
| WO | | WO9307924 | A1 | 4/1993 |
| WO | | 1998017331 | A1 | 4/1998 |
| WO | | WO03072156 | A1 | 9/2003 |
| WO | | 2008006097 | A2 | 1/2008 |
| WO | | 2010001325 | A2 | 1/2010 |
| WO | | 2010057142 | A2 | 5/2010 |
| WO | | 2010094968 | A2 | 8/2010 |
| WO | | 2014041508 | A1 | 3/2014 |
| WO | | WO2014/041508 | * | 3/2014 ............ A01N 37/46 |
| WO | | 2016025407 | A1 | 2/2016 |

OTHER PUBLICATIONS

Vanderah, David J., et al. "Synthesis and Characterization of Self-Assembled Monolayers of Alkylated 1-Thiahexa (ethylene oxide) Compounds on Gold." Langmuir 14:6919-6923, 1998.

Veiseh, Mandana et al., "Guided cell patterning on gold-silicon dioxide substrates by surface molecular engineering", Biomaterials, 25, (2004), pp. 3315-3324.

Vos, Johannes G. et al., "Formation and Characterization of Modified Surfaces", Supramolecular Assemblies, John Wiley & Sons, Ltd., (2003), pp. 87-152.

Xiao, Shou-Jun, et al. "Covalent Attachment of Cell-Adhesive, (Arg-Gly-Asp)-Containing Peptides to Titanium Surfaces." Langmuir 14:5507-5516, 1998.

Zhu, B. et al., "Chain-length dependence of the protein and cell resistance of oligo(ethylene glycol)-terminated self-assembled monolayers on gold", J Biomed Mater Res., 56(3), (Sep. 5, 2001), pp. 406-416.

Abdallah, H.I., et al., "Pacemaker contact sensitivity: clinical recognition and management", Ann Thorac Surg., 57 (4), Apr. 1994, pp. 1017-1018.

Au, Sam H., et al. "A New Angle on Pluronic Additives: Advancing Droplets and Understanding in Digital Microfluidics." Langmuir, 27:8586-8594, 2011.

Bain, Colin et al., "Formation of monolayer films by the spontaneous assembly of organic thiols from solution onto gold", J. Am. Chem. Soc., 111(1), 1989, pp. 321-335.

Barth, Andreas. "Review: The Infrared Absorption of Amino Acide Side Chains," Progress in Biophysics & Molecular Biology, 74:141-173, 2000.

Benhabbour, Soumya et al., "Cell adhesion and proliferation on hydrophilic dendritically modified surfaces", Biomaterials, 29, (2008), pp. 4177-4186.

Berger, Manuel. "Biosensors Coated With Sulfated Polysaccharides for the Detection of Hepatocyte Growth Fatctor/Scatter Factor in Cell Culture Medium." Biosensors and Bioelectronics, 26:1706-1709, 2010.

Buxadera-Palomero et al., "Antifouling coatings for dental implants: Polyethylene glycol-like coatings on titanium by plasma polymerization", Biointerphases, vol. 10, No. 2, Jun. 2015 pp. 029505-1 to 029505-11.

Ferringer, T., et al., "Telangiectatic erythematous cutaneous reaction to an implantable cardioverter defibrillator", Am J Contact Dermat., 14(1), (Mar. 2003), pp. 37-40.

Golda et al, "Oxygen plasma functionalization of parylene C coating for implants surface: Nanotopography and active sites for drug anchoring", Materials Science and Engineering C 33 (2013) 4221-4227.

Grinstaff, Mark W. and Meyers, Steven R. "Biocompatible and Bioactive Surface Modifications for Prolonged in Vivo Efficacy." Chem. Rev., 112(3):1-37, Mar. 14, 2012.

Hamilton, Douglas W., et al. "Comparison of the Response of Cultured Osteoblasts and Osteoblasts Outgrown From Rat Calvarial Bone Chips to Nonfouling KRSR and FHRRIKA-Peptide Modified Rough Titanium Surfaces." Research Gate, Journal of Biomedical Materials Research Part B Applied Biomaterials, pp. 517-527, Nov. 2009.

Harder, P, et al., "Molecular Conformation in Oligo(ethylene glycol)-Terminated Self-Assembled Monolayers on Gold and Silver Surfaces Determines their Ability to Resist Protein Adsorption", J. Phys. Chem. B, 102, (1998), pp. 426-436.

Harris et al., "*Staphylococcus aureus* adhesion to titanium oxide surfaces coated with non-functionalized and peptide-functionalized poly(l-lysine)-grafted-poly(ethylene glycol) copolymers", Biomaterials, vol. 25, No. 18, Aug. 2004, pp. 4135-4148.

Herrwerth, Sascha et al., "Factors that Determine the Protein Resistance of Oligoether Self-Assembled Monolayers—Internal

(56) References Cited

OTHER PUBLICATIONS

Hydrophilicity, Terminal Hydrophilicity, and Lateral Packing Density", J. Am. Chem. Soc., 125, (2003), pp. 9359-9366.
Howard, Melissa, et al., "PEGylation of Nanocarrier Drug Delivery Systems: State of the Art", J. Biomed. Nanotechnol. 4, (2008), pp. 133-148.
Hyukjin Lee et al., "Catechol-Grafted Poly(ethylene glycol) for PEGylation on Versatile Substrates", Languir, vol. 26, No. 6, Mar. 16, 2010, ppl 3790-3793.
International Preliminary Report on Patentability issued in PCT/US2015/044525, dated Feb. 23, 2017, 8 pages.
International Search Report and Written Opinion issued in PCT/US2015/015336, dated Jul. 10, 2015, 14 pages.
International Search Report and Written Opinion issued in PCT/US2015/044525, dated Oct. 9, 2015, 10 pages.
International Search Report and Written Opinion issued in PCT/US2016/067409, dated Mar. 29, 2017, 14 pages.
International Search Report and Written Opinion issued in PCT/US2017/037697, dated Aug. 28, 2017, 13 pages.
International Search Report and Written Opinion issued in PCT/US2017/046160, dated Oct. 20, 2017, 15 pages.
Lin, Shaohui et al., "Antifouling Poly(Beta-Peptoid)s", Biomacromolecules, 12(7), (2011), pp. 2473-2582.
Ma, Hongwei et al., ""Non-Fouling" Oligo(ethylene glycol)-Functionalized Polymer Brushes Synthesized by Surface-Initiated Atom Transfer Radical Polymerization", Advanced Materials, 2004, 16(4), (Feb. 17, 2004), pp. 338-341.
Ma, Hongwei, et al., "Surface-Initiated Atom Transfer Radical Polymerizatino of Oligo9ethylene glycol) Methyl Methacrylate from a Mixed Self-Assembled Monolayer on Gold", Advanced Functional Materials, 16, (2006), pp. 640-648.
Maeda, Hatsuo, et al., "Electrochemical Coating with Poly(phenylene oxide) Films Bearing Oligoether Groups as a Tool for Elimination of Protein Adsorption to Electron Surfaces", Analytical Sciences, 15, (Jul. 1999), pp. 633-639.
Mrksich, Using Self-Assembled Monolayers to Understand the Interactions of Man-Made Surfaces with Proteins and Cells, Annual Reviews Biophys. Biomol. Struct. (1996) 25, pp. 55-78.
Needham, D., et al., Polymer-Grafted Liposomes: Physical Basis for the "Stealth" Property:, Journal of Liposome Research, 2(3), (1992), pp. 411-430.
Niebauer, M. J., et al., "Iridium oxide-coated defibrillation electrode: reduced shock polarization and improved defibrillation efficacy", Circulation, 96(10), (Nov. 18, 1997), pp. 3732-3736.
Norma A. Alcantar et al., Polyethylene glycol-coated biocompatible surfaces:, Journal of Biomedical Materials Research, vol. 51, No. 3, Sep. 5, 2000, pp. 343-351.
Olivares-Navarrete, Rene. "Osteoblasts Exhibit a More Differentiated Phenotype and Increased Bone Morphogenetic Protein Production on Titanium Alloy Substrates Than on Poly-Ether-Ether-Ketone." The Spine Journal, 12:265-272, 2012.
Orner, Brendan P. et al., "Arrays for the combinatorial Exploration of Cell Adhesion", J. Am. Chem. Soc., 126, (Aug. 14, 2004), pp. 10808-10809.
Pale-Grosdemange, Formation of Self-Assembled Monolayers by Chemisorption of Derivatives of Oligo(ethylene glycol) of Structure HS(CH2)11(OCH2CH2)mOH on Gold, Journal of American Chemical Society, vol. 113, No. 1, (1991), pp. 12-20.
Park, Ki Dong; et. al. "Bacterial Adhesion on PEG Modified Polyurethane Surfaces." Biomaterials, 19:851-859, 1998.
Patel, Shyam; et. al. "Control of Cell Adhesion on Poly(methyl methacrylate)." Biomaterials, 27:2890-2897, 2006.
Pensa, Evangelina et al., "The Chemistry of the SulfurGold Interface: In Search of a Unified Model", Accounts of Chemical Research, 45(8), (2012), pp. 1183-1192.
Reddy, Shravanthi T., et al. "Micropatterned Surfaces for Reducing the Risk of Catheter-Associated Urinary Tract Infection: An In Vitro Study on the Effect of Sharklet Micropatterned Surfaces to Inhibit Bacterial Colonization and Migration of Uropathogenic *Escherichia coli*." Journal of Endourology, 25(9):1547-1552, Sep. 2011.

Scardino, Andrew J. "Mini Review: Biomimetic Models and Bioinspired for Fouling Control." Biofouling, 27(1):73-86, Jan. 2011.
Schwartz, Zvi, et al. "RGD-Containing Peptide GCRGYGRGDSPG Reduces Enhancement of Osteoblast Differentiation by Poly(L-Lysine)-Graft-Poly(ethylene glycol)-Coated Titanium Surfaces." ResearchGate, Journal of Biomedical Materials Research Part A, pp. 458-472, Mar. 2004.
Singh, Nripen et al., "The role of independently variable grafting density and layer thickness of polymer nanolayers on peptide adsorption and cell adhesion", Biomaterials, 28, (2007), pp. 763-771.
Skoet, R. et al., "Epoxy Contact Dermititis due to Pacemaker Compounds", Cardiology, 99, (2003), 112.
Stouffer, Jan M. et al., "Polymer monolayers prepared by the spontaneous adsorption of sulfur-functionalized polystyrene on gold surfaces", Macromolecules, 21(5), (1988), pp. 1204-1208.
Su, Chiao-Tzu, et al. "A Facile Approach Toward Protein-Resistant Biointerfaces Based on Photodefinable Poly-P-Xylylene Coating." Colloids and Surfaces B: Biointerfaces, 116:727-733, 2014.
Syburra, T. et al., "Gold-coated pacemaker implantation after allergic reactions to pacemaker compounds", Europace, 12(5), (May 2010), pp. 749-750.
Takae, Seiji et al., "Ligand density effect on biorecognition by PEGylated gold nanoparticles: regulated interaction of RCA 120 lectin with lactose installed to the distal end of tethered PEG strands on gold surface", Biomacromolecules, 6 (2), (2005), pp. 818-824.
Takao Hanawa, "A comprehensive review of techniques for biofunctionalization of titanium", Journal of Periodontal & Implant Science, vol. 41, No. 6, pp. 262-272, Jan. 2011.
Tan et al., Surface Engineering and Patterning Using Parylene for Biological Applications, Materials 2010, 3, 1803-1832; doi: 10.3390/ma3031803; ISSN 1996-1944, www.mdpi.com/journal/materials.
Terrill, Roger H. et al., "Structural Evolution of Hexadecanethiol Monolayers on Gold during Assembly: Substrate and Concentration Dependence of Monolayer Structure and Crystallinity", Langmuir, 14, (1998), pp. 845-854.
Tsai, Meng-Yu, et al. "Vapor-Based Multicomponent Coatings for Antifouling and Biofunctional Synergic Modifications." Adv. Funct. Mater., 24:2281-2287, 2014.
Vanderah, David J., et al. "Characterization of a Series of Self-Assembled Monolayers of Alkylated 1-Thiaologo (ethylene oxides) 4-8 on Gold." Langmuir 16:6527-6532, 2000.
International Preliminary Report on Patentability issued in PCT/US2016/067409, dated Jun. 28, 2018, 7 pages.
International Preliminary Report on Patentability issued in PCT/US2017/037697, dated Dec. 27, 2018, 8 pages.
International Preliminary Report on Patentability issued in PCT/US2017/046160, dated Feb. 21, 2019, 9 pages.
Khoo, X. et al. Directed Assembly of PEGylated-Peptide Coatings for Infection-Resistant Titanium Metal. J. Am. Chem. Soc., 131:10992-10997, 2009.
Kotsokechagia, T. et al. PEGylation of Nanosubstrates (Titania) with Multifunctional Reagents: At the Crossroads between Nanoparticles and Nanocomposites. Langmuir, 28:11490-11501, 2012.
Nie, B. et al. A comparative analysis of antibacterial properties and inflammatory responses for the KR-12 peptide on titanium and PEGylated titanium surfaces. RSC Advances, 2017, 7:34321-34330.
S Rahim, M Sasani Ghamsari, S Radiman. "Surface modification of titanium oxide nanocrystals with PEG." Scientia Iranica Transactions F: Nanotechnology, vol. 19(3), 2012, pp. 948-953. (Year: 2012).
Sigma Aldrich. https://www.sigmaaldrich.com/MSDS/MSDS/DisplayMSDSPage.do?country=US&language=en&productNumber=377996&brand=ALDRICH&PageToGoToURL=https%3A%2F%2Fwww.sigmaaldrich.com%2Fcatalog%2Fproduct%2Faldrich%2F377996%3Flang%3Den. Accessed May 21, 2018. 8 pp. (Year: 2018).
Venkatasubbu, G.D. et al. Folate targeted PEGylated titanium dioxide nanoparticles as a nanocarrier for targeted paclitaxel drug delivery. Advanced Powder Technology 24:947-954, 2013.

(56) References Cited

OTHER PUBLICATIONS

Vladkova, T. G. (2010). Surface Engineered Polymeric Biomaterials with Improved Biocontact Properties. Hindawi Publishing Corporation, International Journal of Polymer Science, vol. 2010, 22 pages.

Yamaguchi, S. et al. Sonodynamic therapy using water-dispersed TiO2-polyethylene glycol compound on glioma cells: Comparison of cytotoxic mechanism with photodynamic therapy. Ultrasonics Somochemistry, 18:1197-1204, 2011.

Yoldas, B.E. (1986). Hydrolysis of titanium alkoxide and effects of hydrolytic polycondensation parameters. Journal of Materials Science, 21:1087-1092, 1986.

* cited by examiner

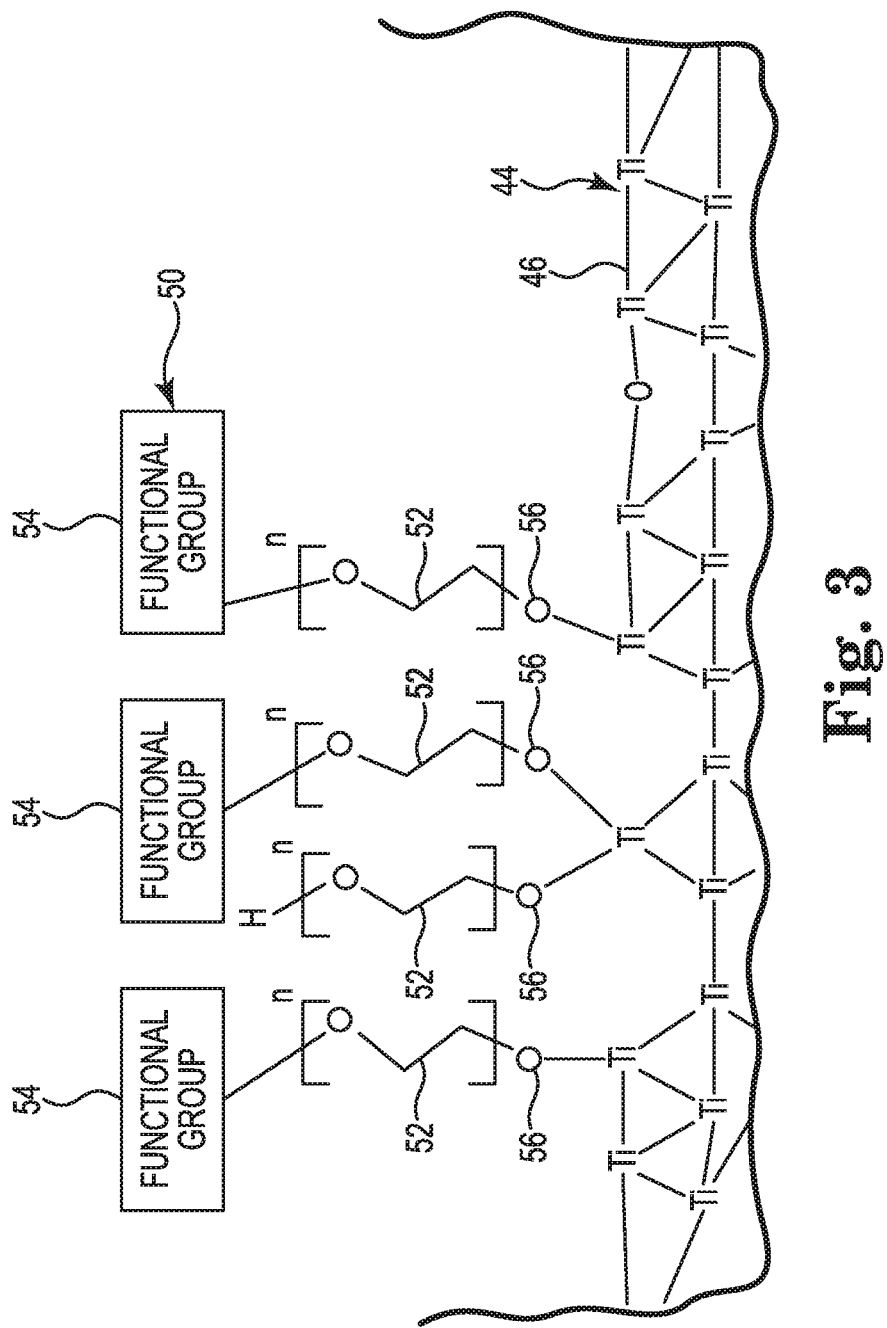

FUNCTIONALIZED PEG FOR IMPLANTABLE MEDICAL DEVICES

CROSS-REFERENCE TO RELATED APPLICATION

This application claims priority to Provisional Application No. 62/372,753, filed Aug. 9, 2016, which is herein incorporated by reference in its entirety.

TECHNICAL FIELD

The present invention relates to coatings and methods for coating implantable medical devices. More specifically, the invention relates to functionalized coatings and methods for producing functionalized coatings for implantable medical devices.

BACKGROUND

Medical devices implanted into a body may be designed such that the device interacts with the body and produces a response, for example, to cause tissue growth around a portion of the medical device to secure the medical device in place. For example, a leadless cardiac pacemaker (LCP) is a medical device implanted into a ventricle of a heart to provide electrophysiological therapy to the heart. The LCP can be contained entirely within the heart. The LCP is self-contained and includes a control systems and a battery so that no leads into the heart are necessary for power or control. The LCP may include tines at a distal end that are designed to penetrate into the cardiac tissue and produce a tissue growth response around the tines to help secure the LCP to the heart wall. The LCP includes an electrode at the distal end designed to be in physical and electrical contact with healthy cardiac tissue to enable efficient and reliable delivery of the therapy. It can be desirable to limit tissue growth around the LCP so that it is easier to remove the LCP once the battery becomes depleted.

Implanting a medical device within a patient inherently exposes the patient to a risk of a nosocomial (e.g. hospital-acquired) infection. The infection can result from bacteria adhering to the exterior surface of the medical device or to tools, such as catheters or stylets, used to implant the medical device.

There is a need for reliable and durable medical device coatings that can function to enhance tissue growth, discourage tissue growth, or reduce the occurrence of nosocomial infections around the medical device after implantation within the body.

SUMMARY

Example 1 is a coating for a metal surface, the coating including poly(ethylene glycol) disposed on and covalently bonded directly to at least a portion of the metal surface, and a functional group grafted to at least a portion of the poly(ethylene glycol). The functional group is one of a bioactive functional group and an antimicrobial functional group.

Example 2 is the coating of Example 1, wherein the poly(ethylene glycol) is covalently bonded directly to the metal surface by an inorganic ether bond.

Example 3 is the coating of either of Examples 1 or 2, wherein the poly(ethylene glycol) covalently bonded directly to the metal surface is a monolayer.

Example 4 is the coating of any of Examples 1-3, wherein the functional group is a bioactive functional group selected from the group consisting of an amino acid derivative and a peptide sequence.

Example 5 is the coating of Example 4, wherein the amino acid derivative is 3,4-dihydroxyphenylalanine and the peptide sequence is arginine-glycine-aspartic acid.

Example 6 is the coating of any of Examples 1-3, wherein the functional group is an antimicrobial functional group selected from the group consisting of chitosan and a silver salt.

Example 7 is an implantable medical device including a metal surface and a coating on the metal surface according to any of Examples 1-6.

Example 8 is the implantable medical device of Example 7, wherein the metal surface includes at least one of a titanium surface, a nitinol surface, and a stainless steel surface.

Example 9 is the implantable medical device of either of Examples 7 or 8, wherein the poly(ethylene glycol) is disposed on a first portion of the metal surface and a second portion of the metal surface, and the functional group grafted to the poly(ethylene glycol) disposed on the first portion is not the same as the functional group grafted to the poly (ethylene glycol) disposed on the second portion.

Example 10 is the Implantable medical device of Examples 7-9, wherein the implantable medical device is a leadless cardiac pacemaker.

Example 11 is a method for coating a metal surface of an implantable medical device. The method includes activating at least a portion of the metal surface by forming hydroxy groups on the metal surface, treating the activated metal surface with a poly(ethylene glycol) to covalently bond the poly(ethylene glycol) directly to the metal surface by inorganic ether bonds, and grafting a bioactive functional group or an antimicrobial functional group to the poly(ethylene glycol) bonded to the metal surface.

Example 12 it the method of Example 11, wherein activating the metal surface includes treating the surface with an oxygen-containing plasma.

Example 13 is the method of either of Examples 11 or 12, wherein the grafting the bioactive functional group to the poly(ethylene glycol) includes treating the poly(ethylene glycol) with succinic anhydride, treating the succinic anhydride treated poly(ethylene glycol) with N-hydroxysuccinimide, and immersing the N-hydroxysuccinimide treated poly(ethylene glycol) with a solution including the bioactive functional group and phosphate buffered saline.

Example 14 is the method of any of Examples 11-13, wherein grafting the bioactive or antimicrobial functional group to the poly(ethylene glycol) includes grafting the bioactive functional group or the antimicrobial functional group to a first portion of the metal surface treated with the poly(ethylene glycol) and grafting the bioactive functional group or the antimicrobial functional group to a second portion of the metal surface. The bioactive functional group or the antimicrobial functional group grafted to the poly (ethylene glycol) on the second portion is not the same as the bioactive functional group or the antimicrobial functional group grafted to the poly(ethylene glycol) on the first portion.

Example 15 is the method of any of Examples 11-14, wherein the poly(ethylene glycol) has an average molecular weight greater than about 500 grams per mole, and the method further includes heating the metal surface to a temperature between about 60° C. and about 200° C. after treating the activated metal surface to melt away excess poly(ethylene glycol) before grafting the bioactive functional group or the antimicrobial functional group to the poly(ethylene glycol).

Example 16 is a coating for a metal surface of an implantable medical device. The coating includes a poly(ethylene glycol) disposed on at least a portion of the metal surface and a functional group grafted to at least some of the poly(ethylene glycol). The functional group is at least one of a bioactive functional group and an antimicrobial functional group. The poly(ethylene glycol) is covalently bonded directly to the metal surface by an inorganic ether bond.

Example 17 is the coating of Example 16, wherein the poly(ethylene glycol) covalently bonded directly to the metal surface is a monolayer.

Example 18 is the coating of either of Examples 16 or 17, wherein the functional group is a bioactive functional group selected from the group consisting of an amino acid derivative and a peptide sequence.

Example 19 is the coating of Example 18, wherein the amino acid derivative is 3,4-dihydroxyphenylalanine and the peptide sequence is arginine-glycine-aspartic acid.

Example 20 is the coating of either of Examples 16 or 17, wherein the functional group is an antimicrobial functional group selected from the group consisting of chitosan and a silver salt.

Example 21 is the coating of any of Examples 16-20, wherein an average molecular weight of the poly(ethylene glycol) is between about 200 grams per mole and about 20,000 grams per mole.

Example 22 is the coating of any of Examples 16-21, wherein an average molecular weight of the poly(ethylene glycol) is between about 400 grams per mole and about 4,000 grams per mole.

Example 23 is an implantable medical device including a metal surface and a coating on the metal surface. The coating includes a poly(ethylene glycol) disposed on at least a portion of the metal surface and a functional group grafted to at least some of the poly(ethylene glycol). The functional group is at least one of a bioactive functional group and an antimicrobial functional group. The poly(ethylene glycol) is covalently bonded directly to the metal surface by an inorganic ether bond.

Example 24 is the implantable medical device of Example 23, wherein the metal surface includes at least one of a titanium surface, a nitinol surface, and a stainless steel surface.

Example 25 is the implantable medical device of either of Examples 23 or 24, wherein the poly(ethylene glycol) is disposed on a first portion of the metal surface and a second portion of the metal surface, and the functional group grafted to the poly(ethylene glycol) disposed on the first portion is not the same as the functional group grafted to the poly(ethylene glycol) disposed on the second portion.

Example 26 is the implantable medical device of any of Examples 23-25, wherein the implantable medical device is a leadless cardiac pacemaker.

Example 27 is the implantable medical device of any of Examples 23-26, wherein the poly(ethylene glycol) covalently bonded directly to the metal surface is a monolayer.

Example 28 is the implantable medical device of any of Examples 23-27, wherein the functional group is a bioactive functional group selected from the group consisting of an amino acid derivative and a peptide sequence.

Example 29 is the implantable medical device of Example 28, wherein the amino acid derivative is 3,4-dihydroxyphenylalanine and the peptide sequence is arginine-glycine-aspartic acid.

Example 30 is the implantable medical device of any of Examples 23-27, wherein the functional group is an antimicrobial functional group selected from the group consisting of chitosan and a silver salt.

Example 31 is a method for coating a metal surface of an implantable medical device. The method includes activating at least a portion of the metal surface by forming hydroxy groups on the surface, treating the activated metal surface with a poly(ethylene glycol) to covalently bond the poly(ethylene glycol) directly to the metal surface by inorganic ether bonds, and grafting a bioactive functional group or an antimicrobial functional group to the poly(ethylene glycol) bonded to the metal surface.

Example 32 is the method of Example 31, wherein activating the metal surface includes treating the surface with an oxygen-containing plasma.

Example 33 is the method of either of Examples 31 or 32, wherein the grafting the bioactive functional group to the poly(ethylene glycol) includes treating the poly(ethylene glycol) with succinic anhydride, treating the succinic anhydride treated poly(ethylene glycol) with N-hydroxysuccinimide, and immersing the N-hydroxysuccinimide treated poly(ethylene glycol) with a solution including the bioactive functional group and phosphate buffered saline.

Example 34 is the method of any of Examples 31-33, wherein grafting the bioactive functional group or the antimicrobial functional group to the poly(ethylene glycol) includes grafting the bioactive functional group or the antimicrobial functional group to a first portion of the metal surface treated with the poly(ethylene glycol), and grafting the bioactive functional group or the antimicrobial functional group to a second portion of the metal surface. The bioactive functional group or the antimicrobial functional group grafted to the poly(ethylene glycol) on the second portion is not the same as the bioactive functional group or the antimicrobial functional group grafted to the poly(ethylene glycol) on the first portion.

Example 35 is the method of any of Examples 31-34, wherein the poly(ethylene glycol) has an average molecular weight greater than about 500 grams per mole, and the method further includes heating the metal surface to a temperature between about 60° C. and about 200° C. after treating the activated metal surface to melt away excess poly(ethylene glycol) before grafting the bioactive functional group or the antimicrobial functional group to the poly(ethylene glycol).

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3 is a cross-sectional schematic diagram of a coating applied to the implantable medical device of FIG. 2, in accordance with embodiments of the disclosure.

Figure 1:
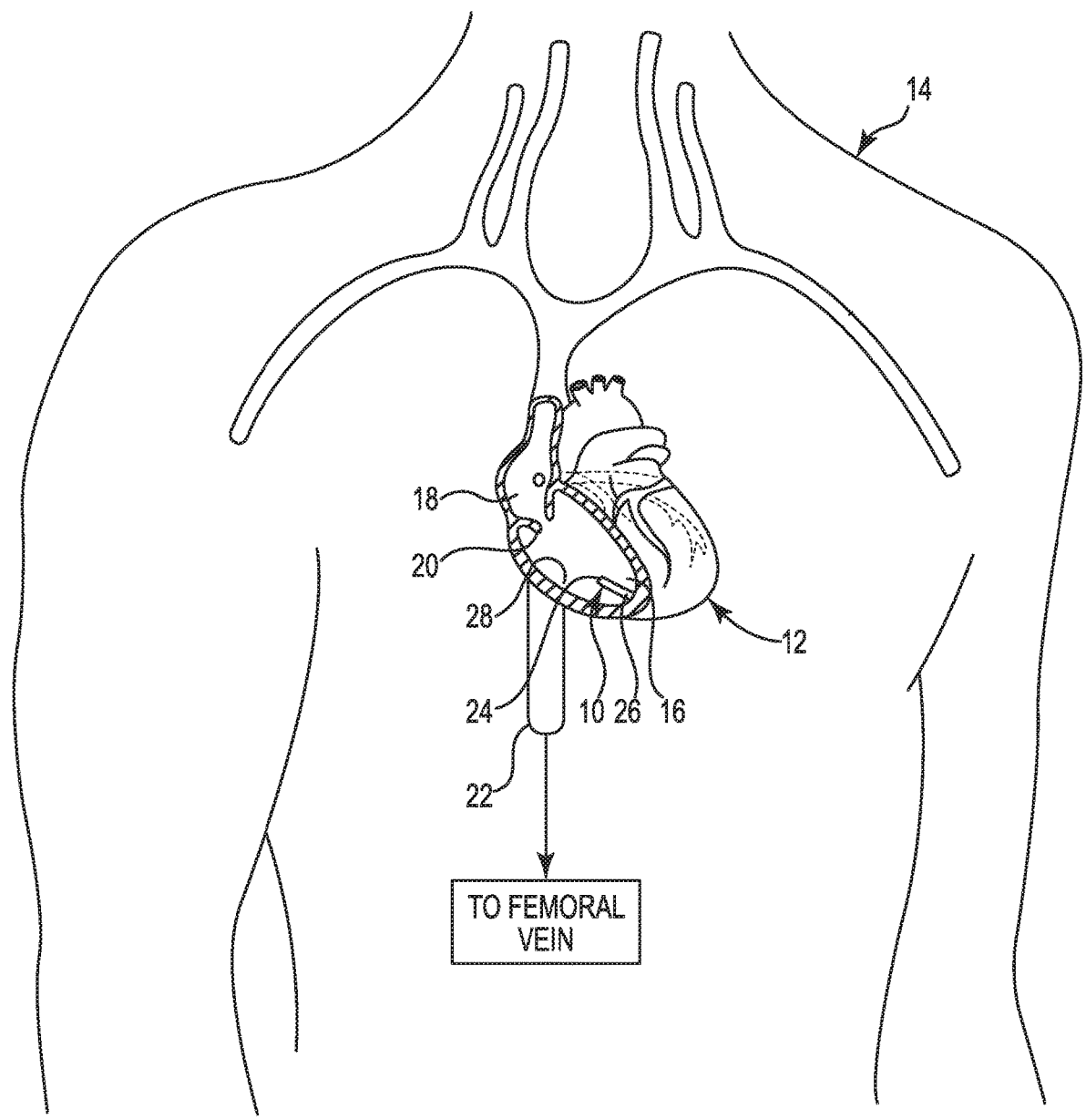
FIG. 1 is a schematic illustration of an implantable medical device in accordance with embodiments of the disclosure implanted within a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

Embodiments of this disclosure include a coating including functional groups linked to a metal surface of an implantable medical device by poly(ethylene glycol) (PEG) bonded to the metal surface. The coating is immobilized and durable because the poly(ethylene glycol) is attached directly to the metal surface by covalent bonds. In some embodiments, the functional groups can be bioactive functional groups or antimicrobial functional groups. Bioactive functional groups are functional groups able to control interactions with proteins to encourage attachment and growth of healthy tissue. In some embodiments, the functional groups can be antimicrobial functional groups that inhibit the growth of microorganisms, such as bacteria, viruses or fungi.

In accordance with various aspects of the disclosure, a medical device is defined as "an implantable medical device" if it is totally or partly introduced, surgically or medically, into the human body or by medical intervention into a natural orifice, and which is intended to remain after the procedure. Implantable medical devices can include a leadless cardiac pacemaker, as discussed below. However, it is understood that the various embodiments can be implemented in any implantable medical device implanted in a patient. Other such implantable medical devices include, without limitation, cardioverter-defibrillator or cardiac resynchronization therapy devices, endocardial leads, epicardial leads, left atrial appendage occlusion devices, neurostimulation systems such as spinal cord stimulation or deep brain stimulation device housings and associated leads, and implantable drug pumps, to name a few.

FIG. 1 provides an illustrative but non-limiting example of an implantable medical device in accordance with the disclosure. The application and location are illustrative only, as implantable medical devices incorporating embodiments of the present invention may be used in a variety of anatomical locations and for a variety of additional purposes.

FIG. 1 illustrates an implantable medical device (IMD) 10 in the form of a leadless cardiac pacemaker (LCP) implanted in a heart 12 of a patient 14. As shown in FIG. 1, the heart 12 includes a right ventricle 16, a right atrium 18, and a tricuspid valve 20 separating the right atrium 18 from the right ventricle 16. An inferior vena cava 22 leads to the right atrium 18. As shown in FIG. 1, in some embodiments the IMD 10 can be implanted in the right ventricle 16. The IMD 10 may be implanted by way of a catheter (not shown) percutaneously entering a femoral vein (not shown) and extending through external and common iliac veins (not shown), the inferior vena cava 22 into the right atrium 18, and through the tricuspid valve 20 into the right ventricle 16. The IMD 10 can have a proximal end 24 and a distal end 26. The IMD 10 can be implanted such that the proximal end 24 is nearest the tricuspid valve 20 and the distal end 26 is in contact with an endocardium 28 lining the walls of the right ventricle 16. Once the IMD 10 is implanted, the catheter (not shown) is withdrawn and the implanted IMD 10 can provide electrophysiological therapy to the heart 12.

Figure 2:
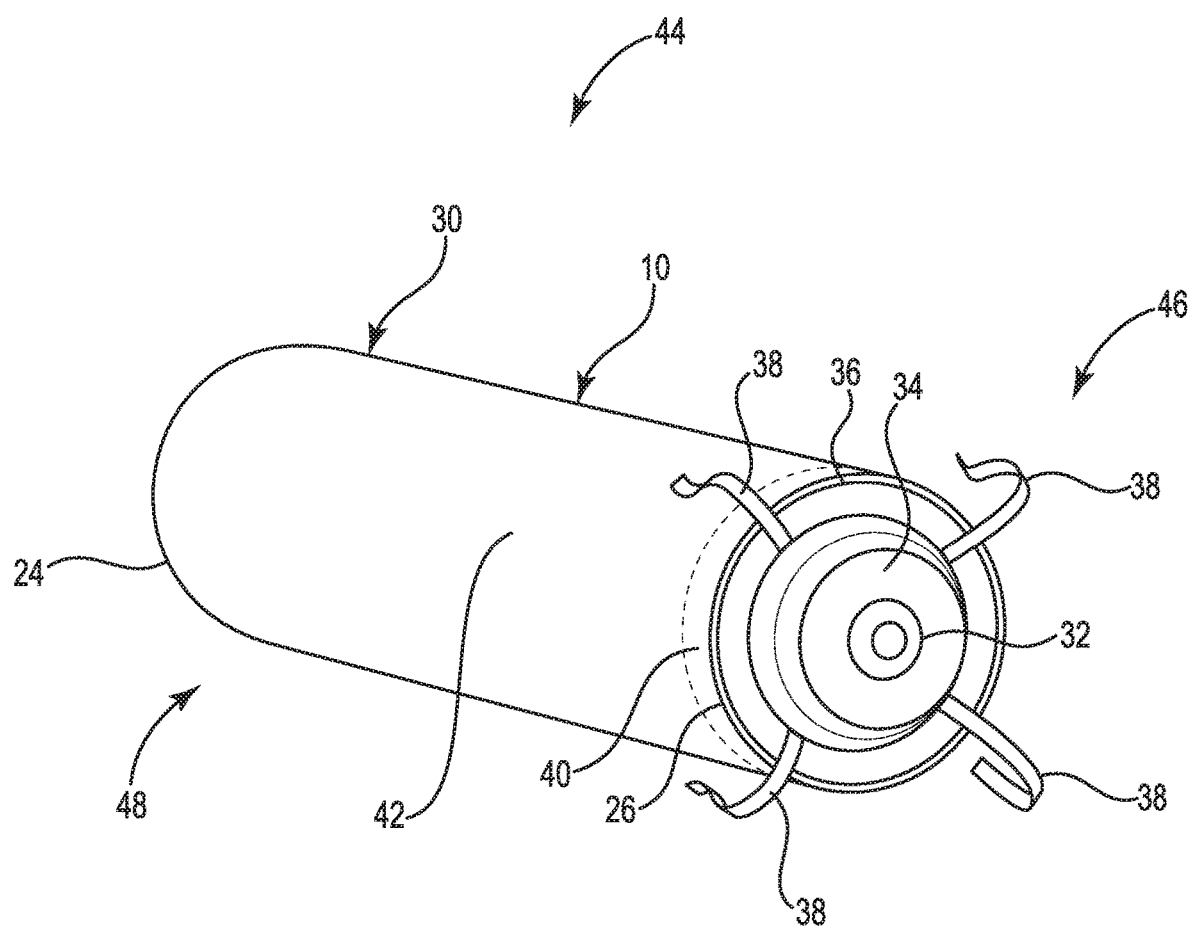
FIG. 2 is a perspective view of the implantable medical device of FIG. 1 in accordance with embodiments of the disclosure.

FIG. 2 is a perspective view of the implantable medical device of FIG. 1 in accordance with embodiments of the disclosure. In the embodiment shown in FIG. 2, the IMD 10 includes a case 30, an electrode 32, an electrode insulator 34, a case insulator 36, and a plurality of tines 38 (4 shown). The case 30 has a roughly cylindrical shape and extends from the proximal end 24 to the distal end 26. The case 30 can house control and communication electronics (not shown) and a battery (not shown). The case 30 can be formed of a biocompatible metal, for example, titanium or stainless steel. In some embodiments, the electrode 32 can be formed of a biocompatible metal, for example, titanium, iridium, gold, or stainless steel. The plurality of tines 38 can be formed of a flexible, resilient, biocompatible metal, for example, nitinol. The electrode 32 and the plurality of tines 38 are disposed at the distal end 26. The electrode insulator 34 is disposed between the electrode 32 and the plurality of tines 38 to electrically insulate the electrode 32 from the plurality of tines 38. The case insulator 36 is disposed between the case 30 and the tines 38 to electrically insulate the case 30 from the tines 38. The electrode insulator 34 and the case insulator 36 may be formed of any biocompatible insulating polymer, such as a fluoropolymer or a silicone.

Once implanted in the heart 12 (FIG. 1), the IMD 10 can be held in place by the plurality of tines 38 which penetrate through the endocardium 28 and into cardiac tissue. It has been found that it may be desirable to encourage cardiac tissue ingrowth around the plurality of tines 38 to more reliably secure the IMD 10 to the heart 12. In some embodiments, the case 30 can include a distal case portion 40 near the distal end 26, and a proximal case portion 42 extending from the distal case portion 40 to the proximal end 24. In some embodiments, it may be desirable to encourage cardiac tissue ingrowth around the distal case portion 40 to more reliably secure the IMD 10 to the heart 12.

In operation, the IMD 10 provides electrophysiological therapy with electrical impulses conducted to the heart 12 through the electrode 32. It has been found that it may be desirable to promote the ingrowth of healthy cardiac tissue around the electrode 32 to more reliably and efficiently conduct the electrical impulses. If scar tissue forms around the electrode 32, the electrical impulses may not conduct reliably or efficiently because, in contract to healthy tissue, scar tissue is collagen-rich and has high impedance.

In some embodiments, it may also be desirable to limit tissue ingrowth on the proximal case portion 42 so that it is easier to remove the IMD 10 once the battery becomes depleted. Considering the embodiment of FIG. 2, the IMD 10 includes a metal surface 44 which includes a first portion 46 in which tissue ingrowth is desired and a second portion 48 in which tissue ingrowth is not desired. The metal surface 44 includes the case 30, the electrode 32, and the plurality of tines 38. The first portion 46 includes the distal case portion 40, the electrode 32, and the plurality of tines 38.

The second portion 48 includes the proximal case portion 42. In some embodiments, a coating 50, as described below in reference to FIG. 3, is disposed on the first portion 46 of the metal surface 44 to promote cell growth and attachment of healthy cardiac tissue to the first portion 46.

FIG. 3 is a cross-sectional schematic diagram of the coating 50 applied to the embodiment of FIG. 2. As shown in FIG. 3, the coating 50 includes poly(ethylene glycol) 52 disposed on the first portion 46 of the metal surface 44, and a functional group 54 covalently bonded, or grafted, to at least a portion of the poly(ethylene glycol) 52. In the illustrated embodiment, the metal surface 44 is a titanium surface including a plurality of native oxide titanium-oxide bonds as well as titanium-titanium bonds. The poly(ethylene glycol) 52 is covalently bonded directly to the metal surface 44 by an inorganic ether bond 56. An inorganic ether bond is an ether bond that covalently bonds an organic molecule to an inorganic surface. In some embodiments, the functional group 54 can be a bioactive functional group that promotes the cell growth and attachment of healthy cardiac tissue. Examples of bioactive functional groups that promote cell growth and attachment of healthy cardiac tissue include amino acid derivatives, such as 3,4-dihydroxyphenylalanine (DOPA), peptide sequences, such as the tripeptide arginine-glycine-aspartic acid (RGD), vascular endothelial growth factor (VEGF), fribronectin, human serum albumin, bovine serum albumin (BSA), fetal calf serum (FCS), platelet-derived growth factor (PDGF), and epidermal growth factor (EGF), to name a few. As shown in FIG. 3, the coating 50 including the functional group 54 is immobilized and durable because the poly(ethylene glycol) 52 is bonded directly to the metal surface 44 by the inorganic ether bond 56.

Figure 4A:
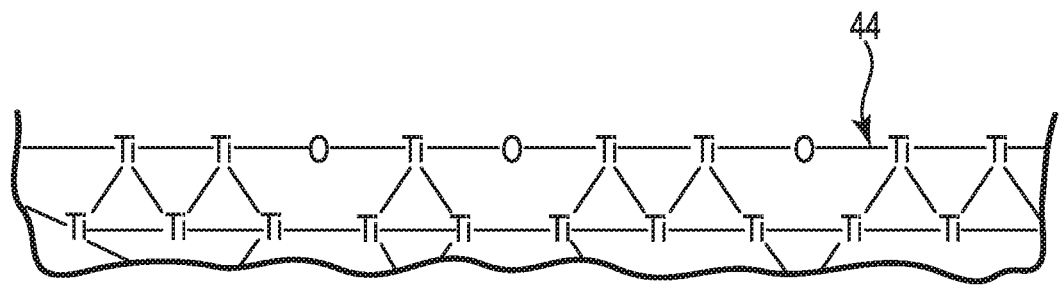
FIGS. 4A-4F are cross-sectional schematic diagrams illustrating a method of forming a coating on the implantable medical device of FIG. 2, in accordance with embodiments of the disclosure.
Figure 4B:
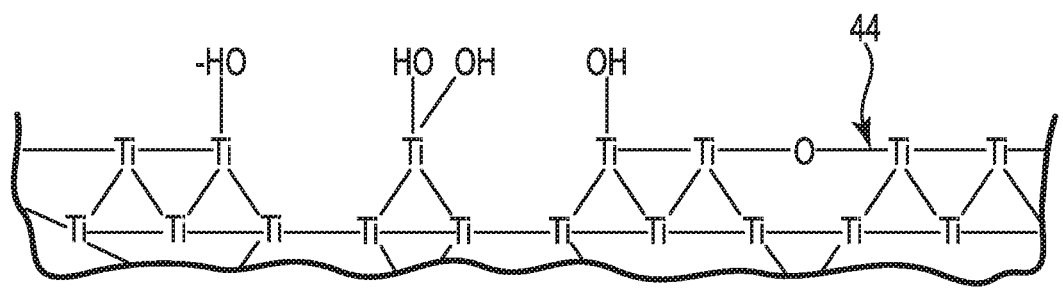

FIGS. 4A-4F are cross-sectional schematic diagrams showing a method of forming the coating 50 on the metal surface 44 of the IMD 10, in accordance with embodiments of the disclosure. FIG. 4A shows cross-section of the metal surface 44 prior to formation of the coating 50. In the illustrated embodiment, the metal surface 44 is a titanium surface including a plurality of native oxide titanium-oxide bonds as well as titanium-titanium bonds. FIG. 4B shows the metal surface 44 following activation of the metal surface 44 with an oxygen-containing plasma treatment. As shown in FIG. 4B, at least some of the titanium-oxide bonds are cleaved by the oxygen-containing plasma, forming reactive hydroxy groups on the metal surface 44 when subsequently exposed to atmospheric moisture. In other embodiments, the oxygen-containing plasma may also include water, forming the reactive hydroxy groups in situ.

Figure 4C:
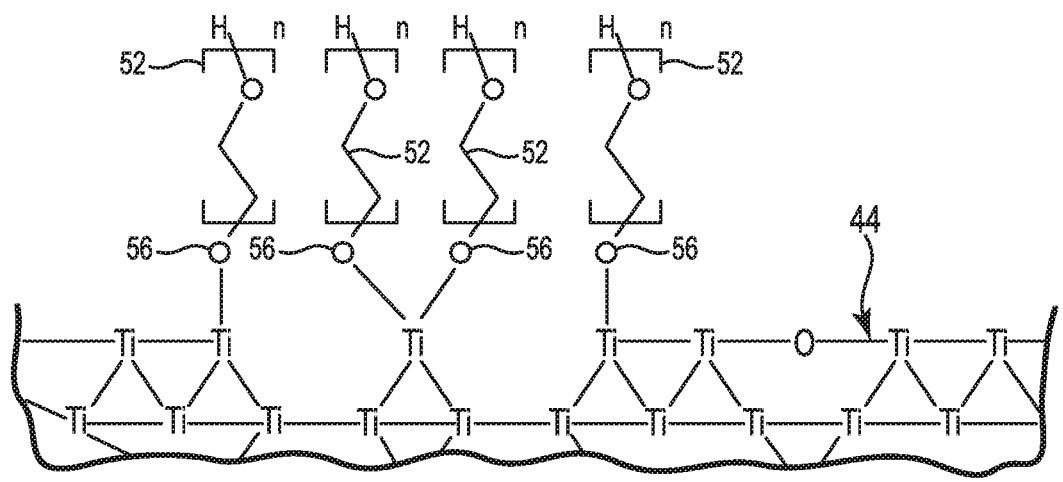

FIG. 4C shows the metal surface 44 after it is treated with hydroxy-terminated poly(ethylene glycol) 52 and before the functional group 54 is grafted to the poly(ethylene glycol) 52 according to Formula I:

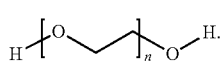

Formula I

As shown in FIG. 4C, the reactive hydroxy groups on the metal surface 44 form covalent inorganic ether bonds with the poly(ethylene glycol) 52. Thus, as shown in FIG. 4C, the poly(ethylene glycol) 52 is covalently bonded directly to the metal surface 44.

The hydroxy groups formed during surface activation are in a high energy, highly reactive state and begin undesired reactions with other hydroxy groups once the metal surface 44 of the IMD 10 is removed from the oxygen-containing plasma. Reacted hydroxy groups are unavailable to form covalent bonds during the treatment step. Thus, in some embodiments, the activated metal surface 44 is treated with the poly(ethylene glycol) 52 within about 72 hours, within about 24 hours, within about 8 hours, within about 4 hour, within about 1 hour, within about 30 minutes, or within about 5 minutes of removal of the IMD 10 from the oxygen-containing plasma.

In some embodiments, the activated metal surface 44 is treated directly with poly(ethylene glycol) 52 by dipping at least a portion of the metal surface 44 in liquid poly(ethylene glycol) 52. In other embodiments, the activated metal surface 44 may be treated by spraying the poly(ethylene glycol) 52 on to at least a portion of the metal surface 44. Other suitable techniques may include inkjet printing, roll coating, screen printing, and microcontact printing the poly(ethylene glycol) 52 on to the activated metal surface 44 on the IMD 10.

In some embodiments, the average molecular weight of the poly(ethylene glycol) 52 may be as low as about 200 grams per mole (g/mole), about 400 g/mole, about 1,000 g/mole, about 2,000 g/mole, or about 3,000 g/mole, or as high as, about 4,000 g/mole, about 8,000 g/mole, about 12,000 g/mole, about 16,000 g/mole, or about 20,000 g/mole, or an average molecular weight within any range defined between any pair of the foregoing values. In some embodiments, the poly(ethylene glycol) 52 may have an average molecular weight from about 200 to 20,000 g/mole, about 400 to about 16,000 g/mole, about 1,000 to about 12,000 g/mole, about 2,000 to about 8,000 g/mole, or about 3,000 to about 4,000 g/mole. In some embodiments, the poly(ethylene glycol) 52 may have an average molecular weight of about 400 g/mole. In some other embodiments, the poly(ethylene glycol) 50 may have an average molecular weight of about 3,350 g/mole.

In some embodiments, the poly(ethylene glycol) 52 may have an average molecular weight low enough that the poly(ethylene glycol) 52 is a liquid at room temperature. For the purposes of this disclosure, room temperature is any temperature ranging from about 18° C. to about 30° C. In such embodiments, poly(ethylene glycol) 52 may have an average molecular weight no greater than about 500 g/mole. For example, poly(ethylene glycol) 52 having an average molecular weight of about 400 g/mole is liquid at room temperature. In such embodiments, after the activated metal surface 44 is treated with the poly(ethylene glycol) 52, excess poly(ethylene glycol) 52 may be allowed to drip off and/or rinsed off with water, leaving behind a monolayer of poly(ethylene glycol) 50 covalently bonded to the metal surface 44 by an ether linkage.

In some other embodiments, the poly(ethylene glycol) 52 may have an average molecular weight high enough that at least some of the poly(ethylene glycol) 52 is in the form of a waxy solid that must be heated above room temperature to be in a liquid form. In such embodiments, the poly(ethylene glycol) 52 may have an average molecular weight greater than about 500 g/mole. In some embodiments, the poly(ethylene glycol) 52 may have an average molecular weight greater than about 1000 g/mole. In embodiments in which the poly(ethylene glycol) 52 must be heated above room temperature to be in a liquid form, the treated metal surface 44 can be heated to melt away excess poly(ethylene glycol) 52. The melted excess poly(ethylene glycol) 52 is allowed to melt and drip off, leaving behind a monolayer of poly(ethylene glycol) 52 covalently bonded to the metal surface 44 by an ether linkage. In some embodiments, the treated metal surface 44 can be heated to a temperature as low as about 60° C., about 80° C., about 100° C., or about 120° C., or as high as about 140° C., about 160° C., about 180° C., or about 200° C., or a temperature within any range defined between any pair of the foregoing values to melt away excess poly(ethylene glycol) 52. In some embodiments, the treated metal surface 44 may be heated to a temperature between about 60° C. and about 200° C., about 80° C. and about 180° C., about 100° C. and about 160° C., and about 120° C. to about 140° C. In some embodiments, the treated metal surface 44 can be heated to a temperature of about 130° C. to melt away excess poly(ethylene glycol) 52. Additional excess poly(ethylene glycol) 52 may be removed by soaking the treated metal surface 44 in water, and/or rinsing the treated metal surface 44 with water.

Figure 4D:
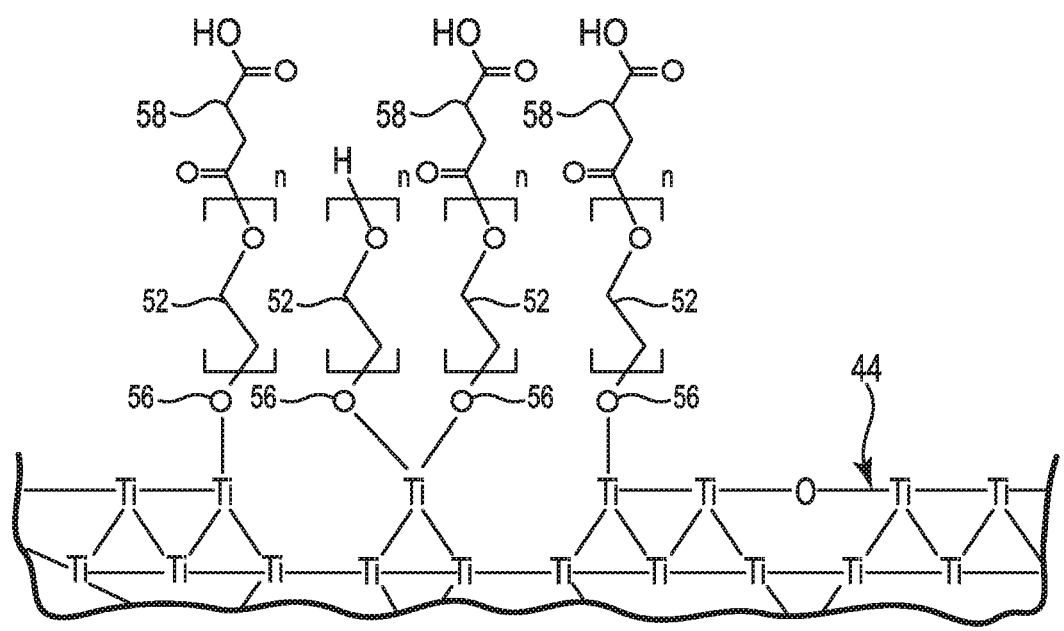

FIG. 4D shows the metal surface 44 after the poly(ethylene glycol) 52 is treated with succinic anhydride 58, according to Formula II:

Formula II

Figure 4E:
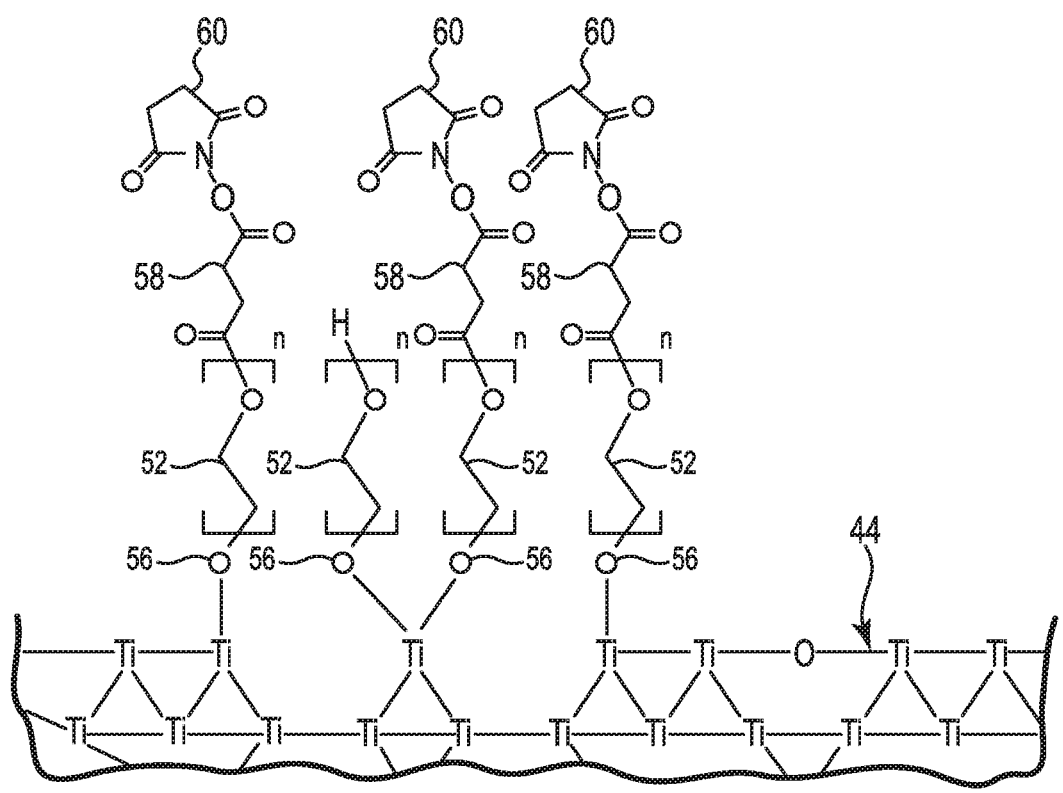

FIG. 4E shows the metal surface 44 after a carboxylic acid group produced by the treatment of the poly(ethylene glycol) 52 with the succinic anhydride 58 is treated with N-hydroxysuccinimide 60 according to Formula III:

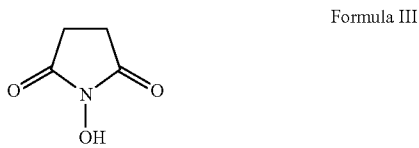

Formula III to create end groups that will couple to free amines in the functional group 54.

Figure 4F:
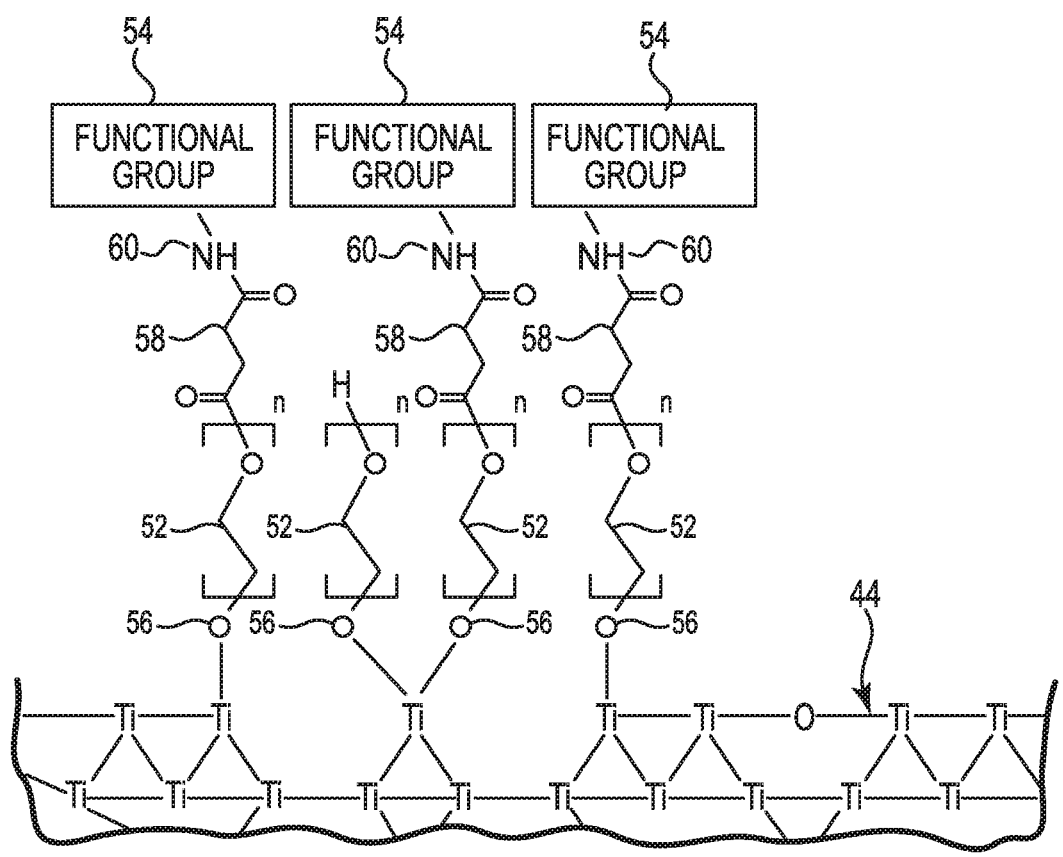

FIG. 4F shows the metal surface 44 after grafting the functional group 54 to the poly(ethylene glycol) 52 by reacting with the end groups created by the N-hydroxysuccinimide 60, according to some embodiments. In some embodiments, such treatment may include, for example, immersing the metal surface 44 in a solution including the functional group 54 and phosphate buffered saline. In some embodiments, the immersion time can be as short as about 2 minutes, about 5 minutes, about 10 minutes, about 20 minutes, or about 30 minutes, or as long as about 40 minutes, about 60 minutes, about 80 minutes, about 100 minutes, or about 120 minutes, or for a time within any range defined between any pair of the foregoing values. In some embodiments, the immersion time can range from about 2 minutes to about 120 minutes, from about 5 minutes to about 100 minutes, from about 10 minutes to about 80 minutes, from about 20 minutes to about 60 minutes, or from about 30 minutes to about 40 minutes. In some embodiments, the immersion is at room temperature.

Figure 5:
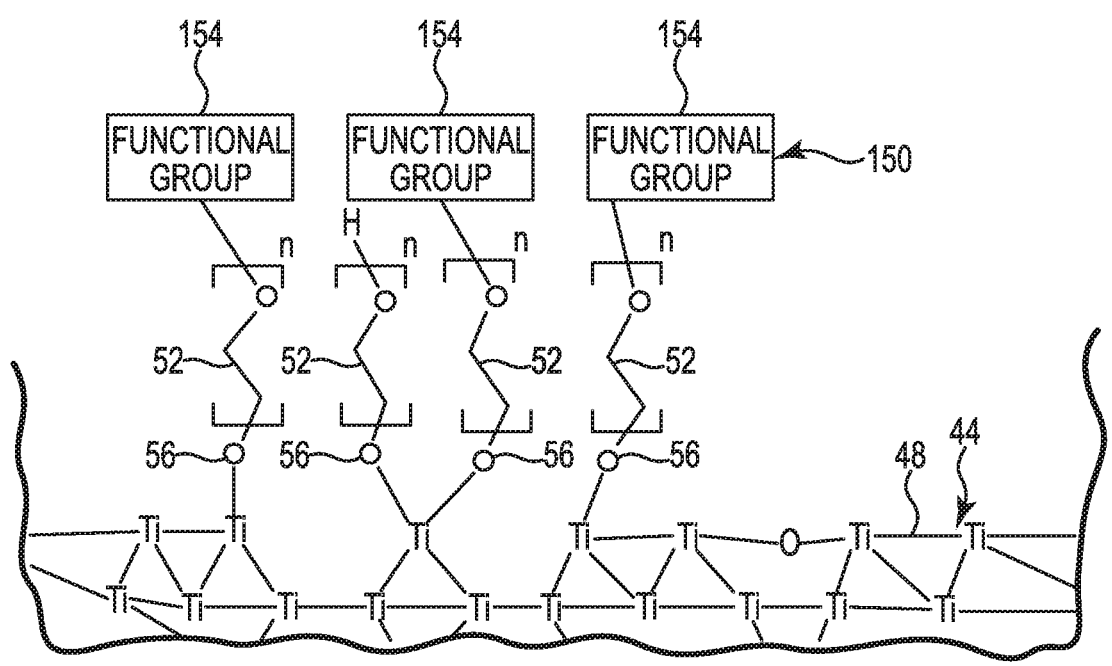
FIG. 5 is a cross-sectional schematic diagram of a coating applied to the implantable medical device of FIG. 2, in accordance with embodiments of the disclosure.

Alternatively or additionally, in some embodiments, a coating 150 can be disposed on the second portion 48 of the metal surface 44 to inhibit the growth of microorganisms, such as bacteria, viruses or fungi. FIG. 5 is a cross-sectional schematic diagram of the coating 150 applied to the embodiment of FIG. 2. As shown in FIG. 5, the coating 150 includes poly(ethylene glycol) 52 disposed on the second portion 48 of the metal surface 44, and a functional group 154 covalently bonded, or grafted, to at least some of the poly(ethylene glycol) 52. As with the embodiment described above in reference to FIG. 3, the metal surface 44 is a titanium surface including a plurality of native oxide titanium-oxide bonds as well as titanium-titanium bonds. The poly(ethylene glycol) 52 is covalently bonded directly to the metal surface 44 by an inorganic ether bond 56 as described above in reference to FIGS. 4A-4C. The functional group 154 can be an antimicrobial functional group that inhibits the growth of microorganisms, such as bacteria, viruses or fungi. Examples of antimicrobial functional groups that inhibit the growth of microorganisms include chitosan and silver salts. As shown in FIG. 5, the coating 150 including the functional group 154 is immobilized and durable because the poly(ethylene glycol) 52 is bonded directly to the metal surface 44 by a covalent bond, the inorganic ether bond 56.

Thus, in some embodiments, in which the poly(ethylene glycol) 52 is disposed on the first portion 46 of the metal surface 44 and the second portion 48 of the metal surface 44, the functional group 54 grafted to the poly(ethylene glycol) 52 disposed on the first portion 46 is not the same as the functional group 154 grafted to the poly(ethylene glycol) 52 disposed on the second portion 48. In this way, the IMD 10 can include a durable, immobilized coating in which some of the functional groups are bioactive functional groups to control interactions with proteins to encourage attachment and growth of healthy tissue, and some functional groups are antimicrobial functional groups that inhibit the growth of microorganisms, such as bacteria, viruses or fungi.

EXAMPLES

The present invention is more particularly described in the following examples that are intended as illustrations only, since numerous modifications and variations within the scope of the present invention will be apparent to those of skill in the art.

Example 1—Water Contact Angle Measurements

The presence of functional groups covalently bonded to titanium surfaces was evaluated by water contact angle measurements. Eight samples of titanium were prepared by cleaning with isopropyl alcohol. The cleaned titanium surfaces were activated with an oxygen plasma for 5 minutes at power of 200 watts and a pressure of 300 mTorr. Seven of the activated samples were treated by dipping them into a 7 wt. % solution of poly(ethylene glycol) (PEG) in water, the PEG having an average molecular weight of 400 grams/mole. The solution was maintained at a temperature of 60° C. and stirred occasionally. The seven samples remained in the solution for 100 minutes to covalently bond the PEG directly to the metal surface by inorganic ether bonds.

Vascular endothelial growth factor (VEGF) functional groups were grafted to two of the PEG coated samples by immersing the samples in a solution of 67 mg of succinic anhydride in 20 milliliters of dimethylformamide (DMF) for one hour at a temperature of 90° C. with occasional stirring. Next, the two samples were immersed in a solution of 40 mg of N-hydroxysuccinimide (NHS) and 50 mg of 1-ethyl-3-(3-dimethylaminopropyl)carbodiimide (EDC) in 20 milliliters of DMF for one hour at a temperature of 90° C. to create end groups that will couple to free amines, as described above. Finally, the two samples were immersed in a solution of VEGF in water at a concentration of 100 nanograms per milliliter for one hour at a temperature of 37° C. to graft the VEGF functional groups to the PEG coated samples.

Vascular endothelial growth factor (VEGF) functional groups were grafted to another two of the PEG coated samples by immersing the samples in a solution of 67 mg of succinic anhydride and 50 mg of EDC in 20 milliliters of DMF for one hour at a temperature of 90° C. with occasional stirring. Next, the two samples were immersed in a solution of 40 mg of N-hydroxysuccinimide (NHS) and 50 mg of 1-ethyl-3-(3-dimethylaminopropyl)carbodiimide (EDC) in 20 milliliters of DMF for one hour at a temperature of 90° C. to create end groups that will couple to free amines, as described above. Finally, the two samples were immersed in a solution of VEGF in water at a concentration of 100 nanograms per milliliter for one hour at a temperature of 37° C. to graft the VEGF functional groups to the PEG coated samples.

Chitosan functional groups were grafted to another two of the PEG coated samples. A chitosan solution was made by dissolving 80 mg of chitosan in a solution of 150 microliters of glacial acetic acid in 10 milliliters of water. Next, one of the two samples received an additional oxygen plasma treatment as described above. Finally, the two samples were immersed in the chitosan solution for one hour at room temperature to graft the chitosan functional groups to the PEG coated samples.

The eight samples, including the one sample that was not PEG coated, were subjected to a water contact angle measurement to determine the presence of the PEG including the functional group. The uncoated sample had a water contact angle that was hydrophobic after a 15 minute soak in phosphate buffered saline. The remaining seven PEG coated samples were all hydrophilic after the 15 minute soak.

Example 2—FTIR Measurements

The presence of functional groups covalently bonded to titanium surfaces was evaluated by fourier transform infrared spectroscopy (FTIR) using a grazing angle of incidence of 84°. Three test groups, T1, T1, and T3, and a control group were prepared by cleaning the titanium with isopropyl alcohol. The three test groups were plasma treated and soaked in a 5 wt. % solution of PEG in water, the PEG having an average molecular weight of 400 grams/mole. The solution was maintained at a temperature of 60° C. and stirred occasionally. The three test groups remained in the solution for 120 minutes to covalently bond the PEG directly to the metal surface.

The two of the test groups, T1 and T2, and the control group were immersed in a solution of 200 mg of succinic anhydride in 50 milliliters of dichloromethane (DCM) for three days at a temperature of 30° C. The remaining test group, T3, was immersed in a solution of 67 mg of succinic anhydride and 50 mg of EDC in 20 milliliters of DMF for one hour at a temperature of 90° C.

Next, test groups T1 and T3, and the control group were immersed in a solution of 40 mg of N-hydroxysuccinimide (NHS) and 50 mg of 1-ethyl-3-(3-dimethylaminopropyl) carbodiimide (EDC) in 20 milliliters of DMF for one hour at a temperature of 90° C. to create end groups that will couple to free amines, as described above. The test group T2 was immersed in a solution of 44 mg of NHS and 20 mg of N,N'-dicyclohexylcarbodiimide (DCC) at room temperature for 12 hours.

Finally, the three test groups and the control group were immersed in a solution of VEGF in water at a concentration of 40 nanograms per milliliter for three hours at a temperature of 37° C. to graft the VEGF functional groups to the PEG coated samples. All test groups and the control group were rinsed in deionized water.

A spectrum of pure VEGF was collected by FTIR spectroscopy using ATR in order to survey for absorbance peaks that could be used to detect the presence of VEGF. A small, sharp peak was observed at 1,260 cm$^{-1}$, most likely attributable to C—O stretching from a tyrosine, glutamic acid, or tyrosine residue. The three test groups, T1, T2, and T3, as well as the control group, were analyzed. No 1,260 cm$^{-1}$ signal was observed for the control group, indicating that no VEGF was bonded to the surface after rinsing. A 1,260 cm$^{-1}$ signal was observed for each of the three test groups, indicating that the VEGF was bonded to the surface, even after rinsing. This suggests that the VEGF was covalently bonded to the titanium surface by the PEG. The 1,260 cm$^{-1}$ was stronger in the T2 group than in the T1 group, and strongest in the T3 group.

Various modifications and additions can be made to the embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A coating for a metal surface of an implantable medical device, the coating comprising:
   a poly(ethylene glycol) disposed on at least a portion of the metal surface, wherein the poly(ethylene glycol) is covalently bonded directly to the metal surface via condensation of hydroxyl groups; and
   a functional group grafted to at least some of the poly (ethylene glycol), wherein the functional group is at least one of a bioactive functional group and an antimicrobial functional group.

2. The coating of claim 1, wherein the poly(ethylene glycol) covalently bonded directly to the metal surface is a monolayer.

3. The coating of claim 1, wherein the functional group is a bioactive functional group selected from the group consisting of an amino acid derivative and a peptide sequence.

4. The coating of claim 3, wherein the amino acid derivative is 3,4-dihydroxyphenylalanine and the peptide sequence is arginine-glycine-aspartic acid.

5. The coating of claim 1, wherein the functional group is an antimicrobial functional group selected from the group consisting of chitosan and a silver salt.

6. The coating of claim 1, wherein an average molecular weight of the poly(ethylene glycol) is between about 200 grams per mole and about 20,000 grams per mole.

7. The coating of claim 1, wherein an average molecular weight of the poly(ethylene glycol) is between about 400 grams per mole and about 4,000 grams per mole.

8. An implantable medical device comprising:
   a metal surface; and
   a coating on the metal surface, the coating including:
   a poly(ethylene glycol) disposed on at least a portion of the metal surface, wherein the poly(ethylene glycol) is covalently bonded directly to the metal surface via condensation of hydroxyl groups; and
   a functional group grafted to at least some of the poly(ethylene glycol), wherein the functional group is at least one of a bioactive functional group and an antimicrobial functional group.

9. The implantable medical device of claim 8, wherein the metal surface includes at least one of a titanium surface, a nitinol surface, and a stainless steel surface.

10. The implantable medical device of claim 8, wherein the poly(ethylene glycol) is disposed on a first portion of the metal surface and a second portion of the metal surface, and the functional group grafted to the poly(ethylene glycol) disposed on the first portion is not the same as the functional group grafted to the poly(ethylene glycol) disposed on the second portion.

11. The implantable medical device of claim 8, wherein the implantable medical device is a leadless cardiac pacemaker.

12. The implantable medical device of claim 8, wherein the poly(ethylene glycol) covalently bonded directly to the metal surface is a monolayer.

13. The implantable medical device of claim 8, wherein the functional group is a bioactive functional group selected from the group consisting of an amino acid derivative and a peptide sequence.

14. The implantable medical device of claim 13, wherein the amino acid derivative is 3,4-dihydroxyphenylalanine and the peptide sequence is arginine-glycine-aspartic acid.

15. The implantable medical device of claim 8, wherein the functional group is an antimicrobial functional group selected from the group consisting of chitosan and a silver salt.

16. A method for coating a metal surface of an implantable medical device, the method comprising:
    activating at least a portion of the metal surface by forming hydroxy groups on the surface;
    treating the activated metal surface with a poly(ethylene glycol) to covalently bond the poly(ethylene glycol) directly to the metal surface via condensation of hydroxyl groups; and
    grafting a bioactive functional group or an antimicrobial functional group to the poly(ethylene glycol) bonded to the metal surface.

17. The method of claim 16, wherein activating the metal surface includes treating the surface with an oxygen-containing plasma.

18. The method of claim 16, wherein the grafting the bioactive functional group to the poly(ethylene glycol) includes:
    treating the poly(ethylene glycol) with succinic anhydride;
    treating the succinic anhydride treated poly(ethylene glycol) with N-hydroxysuccinimide; and
    immersing the N-hydroxysuccinimide treated poly(ethylene glycol) with a solution including the bioactive functional group and phosphate buffered saline.

19. The method of claim 16, wherein grafting the bioactive functional group or the antimicrobial functional group to the poly(ethylene glycol) includes:
    grafting the bioactive functional group or the antimicrobial functional group to a first portion of the metal surface treated with the poly(ethylene glycol); and
    grafting the bioactive functional group or the antimicrobial functional group to a second portion of the metal surface, wherein the bioactive functional group or the antimicrobial functional group grafted to the poly(ethylene glycol) on the second portion is not the same as the bioactive functional group or the antimicrobial functional group grafted to the poly(ethylene glycol) on the first portion.

20. The method of claim 16, wherein the poly(ethylene glycol) has an average molecular weight greater than about 500 grams per mole, and the method further includes heating the metal surface to a temperature between about 60° C. and about 200° C. after treating the activated metal surface to melt away excess poly(ethylene glycol) before grafting the bioactive functional group or the antimicrobial functional group to the poly(ethylene glycol).

* * * * *